US012758200B2

(12) United States Patent
Weber et al.

(10) Patent No.: US 12,758,200 B2
(45) Date of Patent: Oct. 13, 2026

(54) BIOPSY SYSTEM

(71) Applicant: Richard Wolf GmbH, Knittlingen (DE)

(72) Inventors: Bernd Claus Weber, Karlsruhe (DE); Friedrich Hähnle, Bretten (DE); Matthias Lambertz, Bretten (DE); Dirk Hüttenberger, Rammelsbach (DE)

(73) Assignee: RICHARD WOLF GMBH, Knittlingen (DE)

( * ) Notice: Subject to any disclaimer, the term of this patent is extended or adjusted under 35 U.S.C. 154(b) by 345 days.

(21) Appl. No.: 18/560,443

(22) PCT Filed: May 10, 2022

(86) PCT No.: PCT/DE2022/200096
§ 371 (c)(1),
(2) Date: Nov. 13, 2023

(87) PCT Pub. No.: WO2022/237942
PCT Pub. Date: Nov. 17, 2022

(65) Prior Publication Data

US 2024/0245392 A1 Jul. 25, 2024

(30) Foreign Application Priority Data

May 14, 2021 (DE) ..................... 10 2021 204 907.9

(51) Int. Cl.

*A61B 10/02* (2006.01)
*A61B 1/00* (2006.01)

(Continued)

(52) U.S. Cl.

CPC ...... *A61B 10/0283* (2013.01); *A61B 1/00186* (2013.01); *A61B 1/042* (2013.01); *A61B 1/043* (2013.01); *A61B 1/0638* (2013.01)

(58) Field of Classification Search

None
See application file for complete search history.

(56) References Cited

U.S. PATENT DOCUMENTS

| | | | |
|---|---|---|---|
| 2005/0203419 A1 | 9/2005 | Ramanujam et al. | |
| 2008/0045859 A1* | 2/2008 | Fritsch ................ | A61B 18/148 600/567 |

(Continued)

FOREIGN PATENT DOCUMENTS

| | | | |
|---|---|---|---|
| CN | 109674438 | A | 4/2019 |
| DE | 10258483 | B3 | 6/2004 |
| EP | 0962185 | A1 | 12/1999 |

*Primary Examiner* — Michael R Bloch
(74) *Attorney, Agent, or Firm* — McGlew and Tuttle, P.C.

(57) ABSTRACT

A biopsy system (1) includes a biopsy element (3) for taking a sample (33) of tissue (41) to be examined from an organic body, and a fluorescence endoscopy element (5). The fluorescence endoscopy element (5) has a distal section (7), where excitation light is coupled out and fluorescence light is coupled in. The distal section (7) of the fluorescence endoscopy element (5) in the biopsy element (3) is axially positionable in a distal position and in a proximal position. The biopsy element (3) has a receiving space (31) for receiving the sample (33) of the tissue (41) to be examined. The receiving space is closed at the distal end in the distal position of the distal portion (7) of the fluorescence endoscopy element (5) and is open at the distal end in the proximal position of the distal portion (7) of the fluorescence endoscopic element (5).

20 Claims, 9 Drawing Sheets

(51) Int. Cl.
*A61B 1/04* (2006.01)
*A61B 1/06* (2006.01)

(56) References Cited

U.S. PATENT DOCUMENTS

| | | | | |
|---|---|---|---|---|
| 2009/0326384 | A1 | 12/2009 | Bigio et al. | |
| 2010/0168610 | A1 | 7/2010 | Lacombe et al. | |
| 2013/0345558 | A1* | 12/2013 | Boppart | G01B 9/02087 600/425 |
| 2014/0023993 | A1* | 1/2014 | Zeng | A61B 18/18 606/9 |
| 2016/0030022 | A1 | 2/2016 | Sheth et al. | |
| 2017/0319186 | A1* | 11/2017 | Van Der Zaag | A61B 5/6848 |

* cited by examiner

BIOPSY SYSTEM

CROSS REFERENCE TO RELATED APPLICATIONS

This application is a United States National Phase Application of International Application PCT/DE2022/200096, filed May 10, 2022, and claims the benefit of priority under 35 U.S.C. § 119 of German Application 10 2021 204 907.9, filed May 14, 2021, the entire contents of which are incorporated herein by reference.

TECHNICAL FIELD

The present invention relates to a biopsy system for taking tissue samples of an organic, preferably human or animal, body, more particularly for cytological investigation. In particular, the present disclosure relates to a fine needle biopsy (FNB) or fine needle aspiration biopsy (FNAB) system.

BACKGROUND

Often, as part of preventive cancer care or after-care, or in case of suspected cancer, by way of an X-ray, CT or ultrasound examination or using another non-invasive imaging method, an abnormality is diagnosed, which is seen, for example, as a shadow in the examination image. There are various reasons for carrying out such an examination, such as precaution (e.g. screening of the lungs of smokers), after-care (e.g. examination of the lungs in the aftercare of colorectal cancer), or an examination for another reason (e.g. investigation of a potentially injured lung after an accident with the incidental finding "round focus").

Frequently the detection of an abnormality is followed by a treatment (therapy). However, a precondition for a targeted and efficient therapeutic intervention or the decision on whether such a therapeutic intervention is necessary in the first place, is clarifying the precise cause of the abnormality in the examination image. This is because the cause of the shadow can be of completely different types, e.g. tumour, infection, granuloma etc. Different causes sometimes require completely different therapeutic procedures (surgical removal, chemotherapy, radiotherapy, hormonal treatment, pharmacological treatment etc.).

Such clarification (i.e. seeking the cause of the abnormal appearance, i.e. the shadow) takes place by way of an ex situ histopathological or cytological examination of the suspicious tissue. For such an examination, a piece of tissue or individual cells from the area of the detected abnormality is/are required.

Such a piece of tissue or tissue cells is/are obtained by way of removing tissue or removing tissue fluid, which is known as a biopsy. In principle there are different possibilities for carrying out the tissue removal. If the procedure is to be less burdensome for the patient, the biopsy can, for example, be performed percutaneously (e.g. CT or ultrasonically-controlled in order to make the suspicious area, from where the samples are to be taken, visible. For this, a thin, long and rigid biopsy needle is pushed from outside through the skin and the underlying tissue into the affected organ to the abnormality in order to take a tissue sample there, on or within the abormality. Usually, hollow needles of different shapes and designs are used in the percutaneous procedure.

Although the images obtained with the usual imaging methods (CT, ultrasound, etc.) allow the visualisation of suspicious tissue, the degree of tissue differentiation is, however, restricted, i.e. the specificity is limited.

An abnormality as such, does stand out relatively clearly, for example through a different colour tone (in CT and US images though a different grey tone) from the surrounding healthy tissue. As a result of this can be comparatively well detected and the desired removal of tissue carried out comparatively simply in that the distal end of the biopsy needle is guided to the centre of the lesion for example.

However, with the usual imaging methods (CT, US etc.), nothing can be said about how or in which way the tissue shown as a shadow has changed, e.g. benignly or malignantly. Thus, for example, in after-care, a lesion already treated in the past can still appear as shadowing in CT images, even though this is only fibrously altered, i.e. non-malignant tissue. A biopsy from the centre of the shadowing and subsequent pathological and/or cytological examination would confirm this diagnosis.

In the CT or US image, a possibly still present residual tumour (due to, for example, insufficient initial treatment) or even a new tumour formation (relapse, newly occurring after the initial treatment) could not be differentiated from surrounding, fibrously altered tissue shown as shadowing, and would thus remain unnoticed.

A single biopsy from the centre of the apparently homogenous abnormality—on the basis of the CT or US image there would initially be no reason to take a biopsy at another location—would thus lead to a serious incorrect assessment, as it would not show the non-differentiable residual tumour or new tumour formation in the CT or US image and, accordingly, the actually required therapy would not be carried out.

With the usual imaging methods (CT, US etc.) it can also not be guaranteed that all the suspicious tissue is actually made visible. As well as the specificity, the sensitivity is also limited. This means that an abnormality that is large enough and its tissue is sufficiently greatly altered stands out relatively clearly as shadowing from the surrounding healthy tissue. In this case, tissue can be taken relatively easily from this area and forwarded for further pathological examination. However, early malignant changes or small malignant changes can often not be shown, or not shown well enough with the usual imaging methods (CT, US etc.). Possibly, any additionally present early malignant changes or small malignant changes that lie, for example, in the marginal area of the abnormality or even outside the abnormality, remain invisible in the CT or US image.

A therapy (based on the histopathological or cytological result of the biopsy from the central area of the shadowing) would therefore be restricted to the area of shadowing and a "safety area" around shadowing. Any early malignant or small malignant changes in the marginal area or outside the shadowing (invisible in the CT or US image), would only be treated inadequately or not treated at all.

In order to resolve this problem, it is known to take a plurality of biopsies from the entire area of the abnormality and also the tissue surrounding the abnormality in order to reduce the risk of overseeing pathologically relevant tissue, that has to be sent for pathological or cytological examination.

However, a plurality of biopsies has many disadvantages and considerably encumbers the patient. An aggravating fact, i.e. encumbering the patient further, is that a good tissue sample (in the sense of meaningful) should be sufficiently large, and therefore the biopsy needle and directly connected thereto also the puncture channel must have a sufficiently large diameter.

In addition, taking many tissue samples is time-consuming, which in addition to placing a strain on the operating person and the treatment costs, also means a further strain on the patient, e.g. long anaesthesia. Added to this in CT-supported tissue removal is the increasing radiation load with increasing time. As the tissue samples all have to be histopathologically and cytologically evaluated, such a procedure is also cost-intensive.

In some cases it is not necessary to carry out a fully-comprehensive histopathological examination of the tissue. For a fully-comprehensive histopathological examination, an entire cylinder of tissue has to be punched out (punch biopsy) or a relatively large piece of tissue excised (excision biopsy) in order to have enough tissue material available for the examination ex situ. However, for some medical diagnoses, this it not necessary. For example, sometimes it only has to be determined whether only benign tissue or also malignant tissue is present in a suspicious area, such as in shadowing in a CT or US. A fine tissue cytological examination of only a few individual cells may then be sufficient. For such examinations, a less traumatic fine-needle biopsy (FNB) or fine-needle aspiration biopsy (FNAB) is typically used. Compared to the excision or punch biopsy, FNB or FNAB is gentler, pain-free and has fewer complications (including less bleeding). Sedation or even anaesthesia is generally not necessary. In addition, as it is gentler, greater areas can be recorded in the sense of "scanning" the organ.

So that the FNB or FNAB takes place more gently, painlessly and with few complications, in the case of FNB or FNAB a fine needle with a diameter of generally less than 1 mm, and therefore thinner than the large needle for the punch biopsy, is introduced percutaneously into the shadow area. However, in the case of highly viscous fluids such as pus and blood, larger needle diameters are also used.

In FNB or FNAB, in the case of FNAB under suction, aspiration ideally takes place in a fan shape in order to obtain tissue material from different regions. During the back and forth movements of the fine needle, cells are peeled off with a sharp distal edge of the cannula and pushed or sucked into the cannula.

Through the fan-like puncturing and the lining up of several puncture fans (made possible by the use of a gentle fine needle), i.e. through obtaining cell material from many different areas from a comparatively large volume, the suspicious tissue area (i.e. the area seen as shadowing in the CT or US), can be more fully examined. Here, more fully means that compared with punch or excision biopsy, the probability is lower that any smaller and initially unseen malignant areas within an otherwise benign shadow are not recorded or biopsied and not pathologically examined. In addition, tissue material can be obtained from the marginal area and areas outside the suspicious area (shadowing) relatively easily, quickly, gently and with less complications.

FNB or FNAB are particularly difficult if malignant tissue is present in only small quantities within a larger area of shadowing. Cells must always be scraped off and taken from all areas of the shadow. This means that the suspicious area (the shadowing) must be closely, i.e. in a relatively narrow puncture cone (slightly changing needle orientation per puncture when moving the needled forwards and back) and completely, i.e. with many puncture cones (many punctures at different positions), examined.

This procedure is (if a really reliable statement about the presence of malignant areas in the region of the shadowing and its marginal area is to be made) associated with a relatively high time expenditure, which is all the higher the larger the volume of shadowing is.

A meaningful pathological evaluation and assessment of the tissue (benign or malignant) can always only be made afterwards ex situ, i.e. after all the tissue has been taken. This in turn means that local assignment is no longer possible, i.e. a statement on from which area (and possibly marginal area) of the shadowing, any malignant cells originate. This would be advantageous if, for example, additional excision or punch biopsies are to be taken specifically from the malignant area in order to achieve a more accurate, namely fully comprehensive histological evaluation in order to find out precisely what type of malignant tissue is involved. Moreover, only the malignant area of the shadowing (and not necessarily the entire area of shadowing) could be treated.

FNB or FNAB also has the difficulty that very often a lot of material is taken from irrelevant tissue areas (i.e. too many benign cells) and too little, possibly even no, tissue from relevant areas (i.e. too few or no malignant cells). Through a high proportion of irrelevant tissue the result can therefore be "watered down" as far as unrecognizability, i.e. too little specificity. Statistically, in the case of a suspected tumour, a repeat of the FNB or FNAB (re-puncture) is necessary in one third of patients, which is time-consuming and expensive as well as being an addition burden on the patient.

SUMMARY

It is therefore an objective of the present disclosure to provide a biopsy system that, with fewer biopsies, allows a diagnosis to be made more quickly, more cost-effectively and in in a manner more gentle on the patient with higher specificity and greater sensitivity.

According to the present disclosure, to solve this task, a biopsy system is provided, wherein the biopsy system comprises a biopsy element for taking a sample of tissue to be examined from an organic body, and a fluorescence endoscopy element, wherein the fluorescence endoscopy element has a distal section with decoupling of stimulation light as well as coupling in of fluorescence light, wherein the distal section of the fluorescence endoscopy element is axially positionable in the biopsy element in a distal position and in a proximal position, wherein for receiving the sample of the tissue to be examined, the biopsy element has a receiving space which in the distal position of the distal section of the fluorescence endoscopy element is distally closed, and in the proximal position of the distal section of the fluorescence endoscopy element is distally opened.

With such a biopsy system, the tissue can already be preselected in situ before actually being take for cytological examination. This means that with the known non-invasive imaging methods (CT, US etc.), undifferentiated suspicious-looking tissue can already been evaluated in situ in a more differentiated manner (e.g. with regard to the malignancy), through which the specificity is increased. With the fluorescence endoscopy element, tissue can be stimulated in situ to fluorescence with stimulation light. The pathological tissue stimulated by means of stimulation light, or an accumulation of bacteria indicating pathological tissue can fluoresce and thus be recognisably located relative to the surrounding healthy tissue. The fluorescence endoscopy can be carried out, for example, by means of a photosensitiser or marker substance (e.g. chlorine e6) which selectively accumulates on pathological material and fluoresces.

Thus, with the fluorescence endoscopy element, actually pathological material can be very precisely localised. When tissue of relevance for the biopsy has been located by way of fluorescence via the fluorescence endoscopy element, the fluorescence endoscopy element can be pulled out of the insertion sleeve, wherein the insertion sleeve remains in the body. The biopsy needle can then be guided through the insertion sleeve precisely to the point where the fluorescence endoscopy element has recognised the tissue to be examined. Therefore, with this biopsy system, in situ more, ideally all relevant, e.g. early malignant and malignant, areas in the organ in question can be localised, without having to take patient-burdening random incidental biopsies from tissue that is not relevant. This means considerably increased sensitivity.

The number or repunctures is greatly reduced with this biopsy system, which makes diagnosis faster, more gentle on the patient and more cost-effective. This is due to the fact that the specificity of the tissue sample can already be checked in situ and thereby "watered down" samples with a too large proportion of non-relevant tissues are not taken in the first place.

Another advantage of this biopsy system is that the risk is reduced of the taken tissue sample, that is examined pathologically or cytologically as a relevant piece of tissue and then determines the subsequent therapeutic procedure, originating from a benign, pathologically irrelevant tissue area.

Preferably, the biopsy system is a system for fine-needle biopsy or fine-needle aspiration biopsy, wherein the biopsy element is a biopsy fine needle. Preferably, the distal section of the fluorescence endoscopy element acts as a suction piston in the biopsy element in order to suck tissue material into the receiving space when the distal section of the fluorescence endoscopy element is moved from the distal position into the proximal position. However, it is also possible to use the biopsy system disclosed here for punch or excision biopsy. Ultimately, FNB or FNAB only differs from the coarser punch or excision biopsy through the thinner biopsy needle and possibly the sucking in of tissue into the biopsy needle.

Optionally, in the distal position the distal section of the fluorescence endoscopy element can completely fill the receiving space. In this way the distal section of the fluorescence endoscopy element can simply act as a suction piston and the biopsy element can be configured to be very thin.

Optionally, the fluorescence endoscopy element can be set up to optionally distally extract stimulation light and inject fluorescence light in the distal position of the distal section of the fluorescence endoscopy element, the proximal position of the distal section of the fluorescence endoscopy element and/or any intermediate position of the distal section of the fluorescence endoscopy element. This is of particular interest in order to immediately be able to check in situ whether malignant tissue really is present in the receiving space. For example, in the distal position of the distal section of the fluorescence endoscopy element a high fluorescence signal is detected by the fluorescence endoscopy element and thereupon, for sucking in tissue, the distal section of the fluorescence endoscopy element is pulled into the proximal position. If, during this, the fluorescence signal weakens, this means that fluorescing tissue has not been sucked into the receiving space. If, by contrast, the fluorescence signal does not weaken or only weakens slightly this is a sure sign that there is fluorescing tissue in the receiving space. This can evaluated not only qualitatively but also quantitatively through the height of the fluorescence signal. Thus, with a defined lower limit for the fluorescence signal, it can be ensured that the tissue sample has a certain specificity.

Optionally, the distal section of the fluorescence endoscopy element can be guided in the biopsy element in a radially sealing manner so that in the receiving space a sucking-in effect into the receiving space is produced during the proximal pulling back of the distal section of the fluorescence endoscopy element in the biopsy element. The distal section of the fluorescence endoscopy element can thus act as a suction piston.

Optionally a distal end of the distal section of the fluorescence endoscopy element in the distal position can close the receiving space in a flush manner with a distal tip of the biopsy element or distally project from the distal tip of the biopsy element. This makes the puncture and forwards movement of the biopsy element gentler in the areas that are currently not to be biopsied. The distal section of the fluorescence endoscopy element can remain in the distal position until a sufficiently strong fluorescence signal is detected. This spares all the benign and healthy tissue that has to be pierced in order to reach the relevant malignant tissue.

Optionally, the distal section of the fluorescence endoscopy element can be locked in the distal position and/or the proximal position relative to the biopsy element. Locking, at least in the distal position make sense so that during the puncture the distal section of the fluorescence endoscopic element is not unintentionally pushed in or has to be held manually. The proximal position can also be determined by locking, but can also be any axial position manually selected by the operator. The length of the receiving space can accordingly be selected by the operator through the proximal position or determined by a stop or lock.

Optionally, the distal section of the fluorescence endoscopy element, at least in the distal position, can be held in in a defined rotational position in a rotationally-fixed manner about its longitudinal axis in the biopsy element. Preferably, the rotational position is defined by a longitudinal bar in a corresponding longitudinal groove. Between the distal position and the proximal position the angular position of the longitudinal bar and/or the longitudinal groove can be different than in the distal or proximal position. Through this, axial locking in the distal or proximal position can be achieved, wherein through turning the distal section of the fluorescence endoscopy element into the other angular position, the lock can be released.

Optionally, a distal end of the distal section of the fluorescence endoscopy element and a distal tip of the biopsy element can be bevelled at the same angle. Preferably, the angle can be acute and preferably be 45° or less.

Optionally, the distal section of the fluorescence endoscopy element and/or the biopsy element can be configured as a disposable article for single use. In this way, the distal section of the fluorescence endoscopy element and/or the biopsy element can be produced particularly thinly and cost-effectively.

Optionally the fluorescence endoscopy element can comprise a light guide with proximal coupling in of stimulation light and/or proximal decoupling of fluorescence light, wherein a distal end of the light guide distally extracts the stimulation light and/or distally couplies in the fluorescence light. This is the preferred embodiment for particularly thin biopsy elements. The light guide itself acts as a suction piston and is guided in a radially sealing manner in a very thin channel of the biopsy element, so that a distal section of channel, when the light guided is retracted, forms the receiving space, which in the distal position is completely filled by the light guide. Here, the light guide can form both an illumination path for the stimulation light and an image patch for the fluorescence light. “Image path” should not be restricted here to an image being produced from the injected fluorescence light. In the image path just an injected fluorescence signal can be transmitted, the property of which is determined.

Optionally, the distal section of the fluorescence endoscopy element can have an LED for decoupling stimulation light and/or an image sensor, a photodiode or similar for coupling in fluorescence light. In combination with a light guide or alternatively the illumination path and/or the image path can be electrical up to the distal section of the fluorescence endoscopy element. An LED at the distal end can emit the stimulation light and the fluorescence light can be taken via a light guide to a proximal image sensor, a photodiode or similar, or taken up by a distal image sensor, a photodiode or similar. Equally, a light guide can guide stimulation light of a proximal LED to the distal section of the fluorescence endoscopy element and extract it there. It is pointed out here, that coupling in of fluorescence light by means of an image sensor, a photodiode or similar, here does not necessarily have to be used to produce images. For deciding whether the fluorescence signal is conspicuous or not, i.e. a biopsy should or should not be taken, it is often enough if only one property of a fluorescence signal, for example its amplitude or intensity, is determined. For example, the conspicuousness can be seen in increased or decreased fluorescence intensity compared to the surrounding tissue or compared to a reference value.

Optionally, the fluorescence endoscopy element can be set up to optionally proximally inject a first stimulation light and/or a second stimulation light, wherein the first stimulation light is on average shorter wave than the second stimulation light, and wherein the fluorescence endoscopy element is set up to optionally produce a first image or a first fluorescence signal of a first tissue area from the first fluorescence light stimulated with the first stimulation light and a second image or a second fluorescence signal from a second tissue area from the second fluorescence light stimulated with the second stimulation light. As the penetration depth of the shorter-wave, first stimulation light is smaller than the penetration depth of the longer-wave second stimulation light, the first tissue area is preferably smaller than the second tissue area. The localisation of pathological tissue thus takes place with a higher spatial resolution by way of the first stimulation light. As the penetration depth of the longer-wave second stimulation light can be greater, the detected fluorescence signal can also originate from an correspondingly larger second tissue area. The localisation of pathological tissue thus takes place with a lower spatial resolution by way of the second stimulation light, but a larger volume is recorded. Therefore, initially a larger, second, tissue area can be preselected more roughly with the longer-wave second stimulation light, and then a smaller, first tissue area, which is preferably a part of the second tissue area can be examined more closely with the shorter-wave, first stimulation light.

Optionally, the fluorescence endoscopy element can have an optical component which is detachably couplable or firmly coupled to the distal section of the fluorescence endoscopy element, wherein the optical component has a beam splitter with an image path side and an illumination path side, wherein to extract the fluorescence light an image sensor, a photodiode or similar is detachably connectable or firmly connected to the image path side, and wherein to inject the stimulation light, a light source is detachably connectable or firmly connected to the illumination path side. The light source is preferably at least an LED or at least one laser decoupling. The beam splitter can, for example, comprise a pair of prisms which together form a beam splitter block that at least largely separates the stimulation light and the fluorescence light so the fluorescence light is transmitted or reflected to the image path side. Vice versa, the pair of prisms can reflect or transmit the stimulation light to the illumination path side. Preferably the image path side and the illumination path side of the beam splitter lie on sides of the beam splitter arranged at an angle, preferably of around 90° to each other. Preferably the image path side lies on the proximal side, so that fluorescence light is essentially transmitted from the distal input side of the beam splitter to the image path side. The illumination path side is preferably on the lateral side so that stimulation light is essentially reflected from the lateral input towards the distal output side.

Optionally, the optical component can have an optical longpass filter which transmits the fluorescence light more strongly to the image path side than the stimulation light, and/or comprises an optical shortpass filter which reflects the fluorescence light more strongly to the image path side than the stimulation light. For example, the longpass filter or the shortpass filter can be arranged between a pair of prisms acting as a beam splitter and/or be in the form of a layer of one or both sides of the prisms facing each other. This is particularly sensible if the stimulation light is shorter wave than the fluorescence light.

Optionally the fluorescence endoscopy element can comprises an operating unit signal-connected or connectable with the image sensor, the photodiode or similar and/or the light source, wherein the operating unit has an optical and/or acoustic display component, a control and supply component and an operating component.

Optionally the optical component can be arranged in a handpiece of the fluorescence endoscopy element to which the distal section of the fluorescence endoscopy element and the biopsy element can be coupled, wherein the handpiece is preferably configured for multiple use. This is sensible as the optical component, possibly with LED and/or image sensor or photodiode or similar can be relatively expensive and the handpiece has no direct contact with the patient. For the biopsy, the distal section of the fluorescence endoscopy element and the biopsy element, which are preferably disposable articles for single use, can then be removed from a sterile package and coupled to the sterile handpiece.

The terms “distally” and “proximally” should herein denote a relative position that is distal or proximal of an operator of the system as a reference position. The terms “distal side” and “proximal side” should herein accordingly mean positions on a distal or proximal side of an object. The terms “distally” and “proximally” should herein denote directions that extend distally and proximally.

The disclosure is explained below in more detail by way of examples of embodiment shown in the drawings. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1:
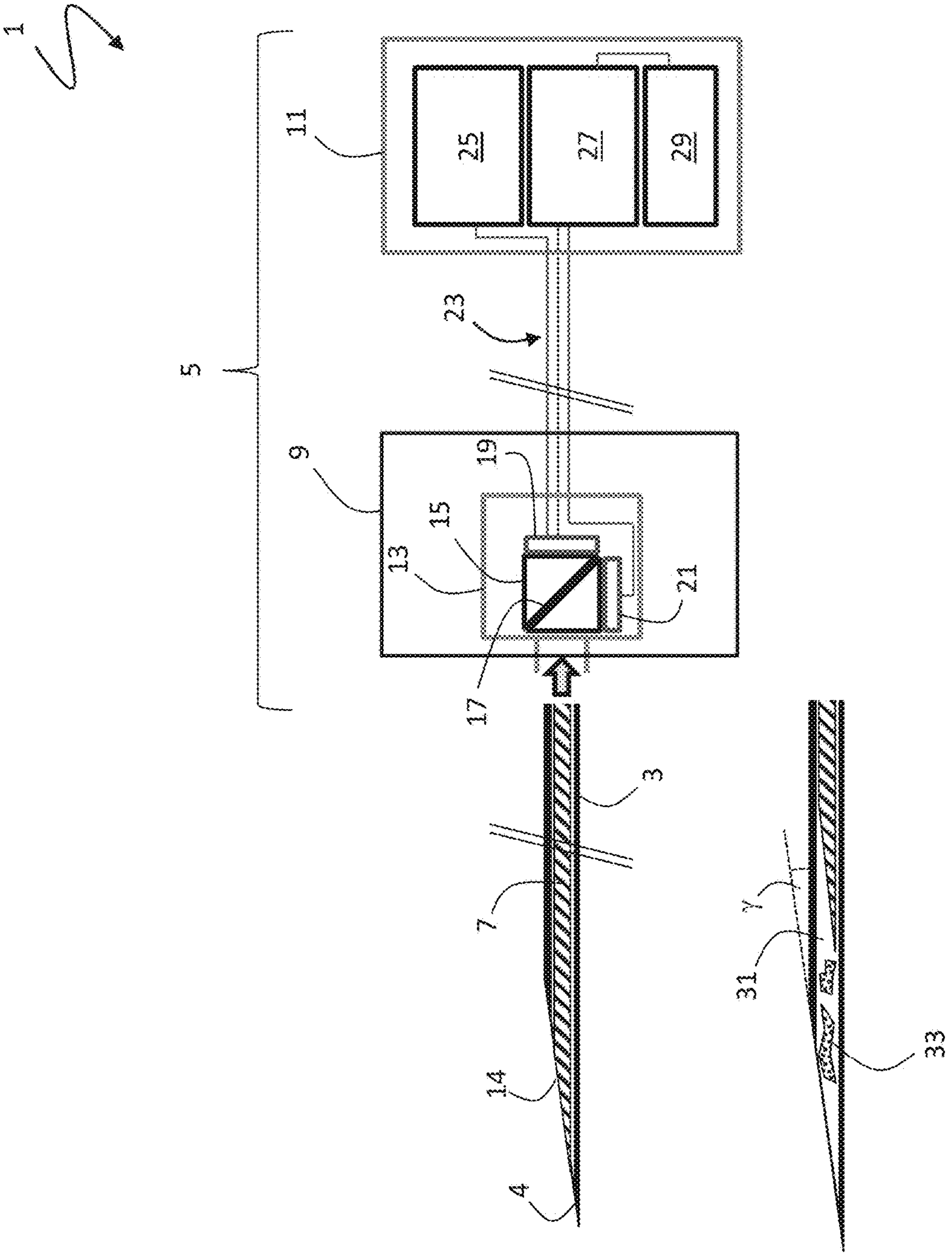
FIG. 1 is a schematic view showing an example of embodiment of a biopsy system disclosed herein.

Referring to the drawings, FIG. 1 shows a biopsy system 1 with a biopsy element 3 in the form of a biopsy fine needle, which is configured as a very thin cannula with, on the distal side, a distal tip 4 bevelled at an acute angle γ. The biopsy system 1 also comprises a fluorescence endoscopy element 5. The fluorescence endoscopy element 5 itself comprises a distal section 7 in the form of a light guide that is passed in a precisely fitting manner through the canula of the biopsy element 3, a handpiece 9 and an operating unit 11. Arranged in the handpiece 9 is an optical component 13, with which the light guide 7 can be detachably coupled or is firmly coupled. For handling by means of the handpiece 9, the biopsy element 3 can be detachably coupled or is firmly coupled to the handpiece 9. Preferably the handpiece 9 is configured for multiple use, whereas the biopsy element 3 as well as the light guide 7 as a pre-assemble element, are configured as disposable articles for single use and for connecting to the handpiece 9.

By coupling the light guide 7 to the optical component 13, proximal decoupling of fluorescence light from the light guide 7 into the optical component 13 as well as proximal coupling in of stimulation light from the optical component 13 into the light guide 7 is achieved. Like the distal tip 4 of the biopsy element 3, a distal end 14 of the light guide is bevelled at the same acute angle γ and can distally close off the cannula of the biopsy element 3 in a flush manner.

The optical component 13 comprises a beam splitter 15 in the form of a beam splitter block which is formed by a pair of prisms. The prisms each adjoin each other with optical interfaces that extend at an angle of approximately 45° relative to the optical axis. Arranged between or at least at or on one of the optical interfaces is a longpass filter 17 which essentially transmits long-wave fluorescence light and reflects short-wave stimulation light. Essentially, coaxially to the optical axis, the beam splitter 15 therefore has an image path side on which an image sensor 19, a photodiode or similar is arranged. Laterally, the beam splitter 15 comprises an illumination path side, on which a light source 21, for example in the form of an LED or a laser decoupling, is arranged. The longpass filter 17 reflects the stimulation light distally to the light guide 7.

The operating unit 11 is signal-connected or signal-connectable to the image sensor 19, the photodiode or similar, and the light source 21 via a cable connection 23. The light source 21 can be controlled via the operating unit 11 and the signals of the image sensor 19, the photodiode or similar, can be received, processed and, if necessary, visualised by the operating unit 11. For this, the operating unit 11 has an optical and/or acoustic display component 25, a control and supply component 27 and an operating component 29.

FIG. 1 shows the biopsy element 3 and the light guide as the distal section 7 of the fluorescence endoscopy element 5 in various axial positions of the light guide 7 relative to the biopsy element 3. At the top the light guide 7 is in a distal position and at the bottom in any proximal position. In the proximal position shown at the bottom, the light guide 7 is proximally retracted, through which in the canula of the biopsy element 3 on the distal side of the light guide 7, a receiving space 31 for receiving tissue samples 33 is formed. Alternatively to the light guide, the distal section 7 of the fluorescence endoscopy element 5 could have distal LED and/or a distal image sensor, a photodiode or similar, and the image path and/or illumination path electrically implemented without the optical component 13.

Figure 2:
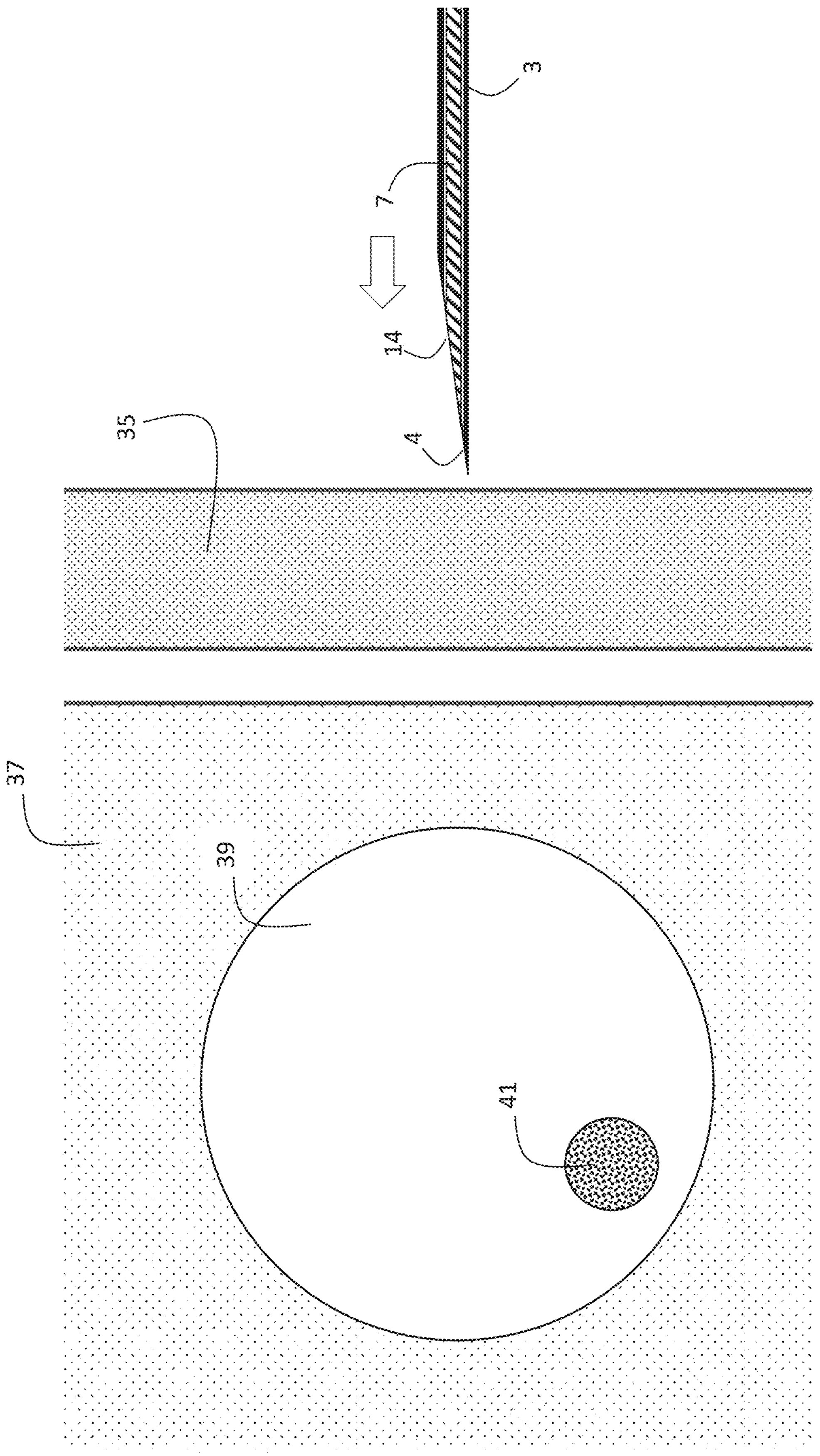
FIG. 2, FIG. 3, FIG. 4, FIG. 5, FIG. 6 and FIG. 7 are schematic views showing the example of embodiment in FIG. 1 in different phases of use.

FIG. 2 schematically shows the biopsy element 3 and the light guide 7 in the distal position shortly before puncturing though the skin 35 of a patient. In the body of the patient is an organ 37 which in the CT image and/or US image shows a relatively large volume of conspicuous shadowing 39. Actually, in this shown example, the majority of the shadowing 39 is benign tissue and only a small part thereof is malignant tissue 41.

Figure 3:
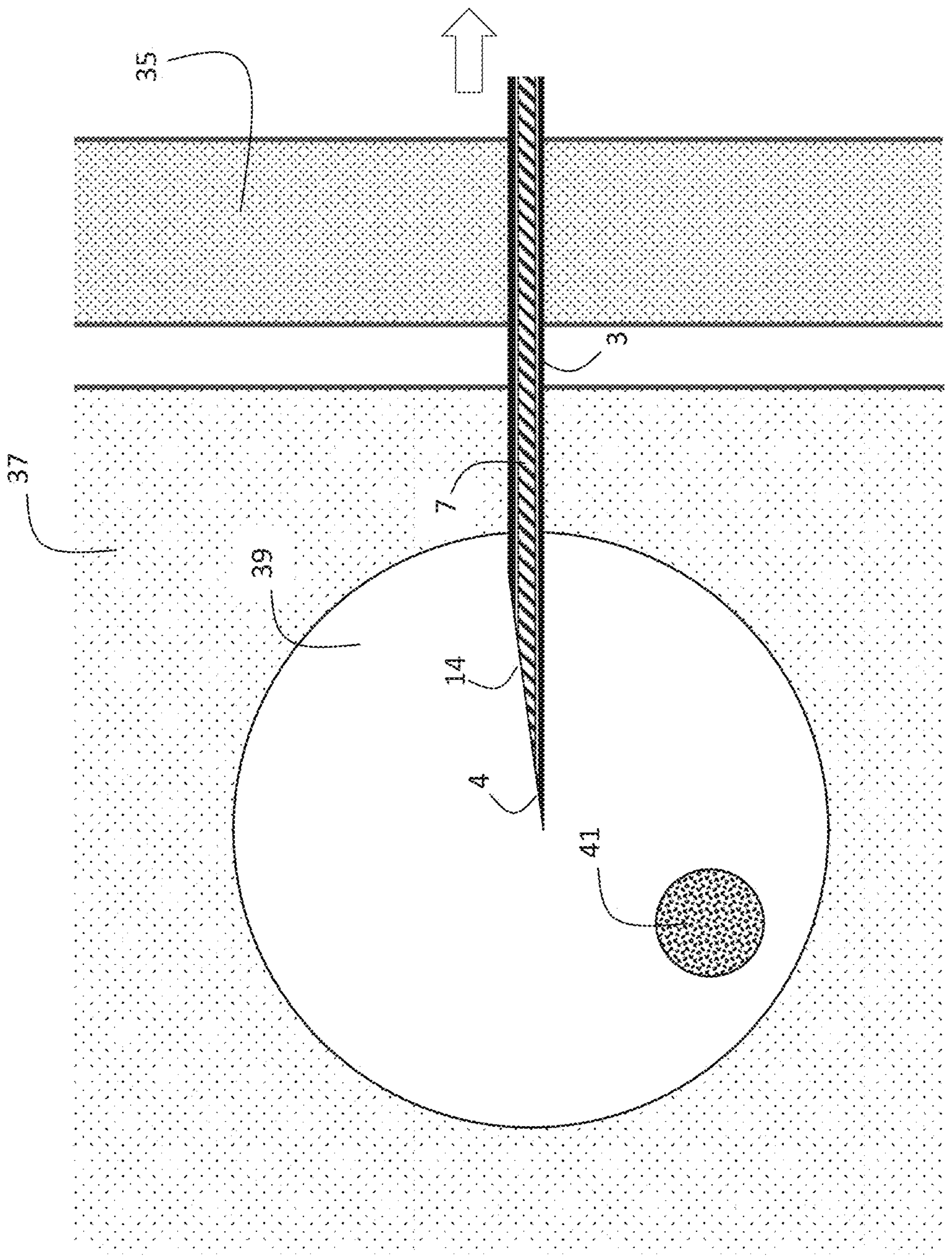

FIG. 3 shows how the biopsy element 3 with the light guide 7 in the locked distal position has been punctured into the shadowing 39 of the organ 37. The puncture is relatively atraumatic as the receiving space 31 is distally closed off by the light guide 7. In this, stimulation light is preferably permanently extracted via the distal end 14 of the light guide 7. Preferably it is also constantly monitored whether a fluorescence signal is being received. As before the biopsy the patient has preferably had a photosensitiser or marker substance (e.g. chlorine e6) administered, malignant tissue should fluoresce conspicuously before the distal end 14 of the light guide 7. As the benign tissue in the shadowing 39 does not fluoresce or only does so inconspicuously, the operator can decide that a biopsy at this point is not sensible and withdraw the biopsy element 3 and the light guide 7 again.

Figure 4:
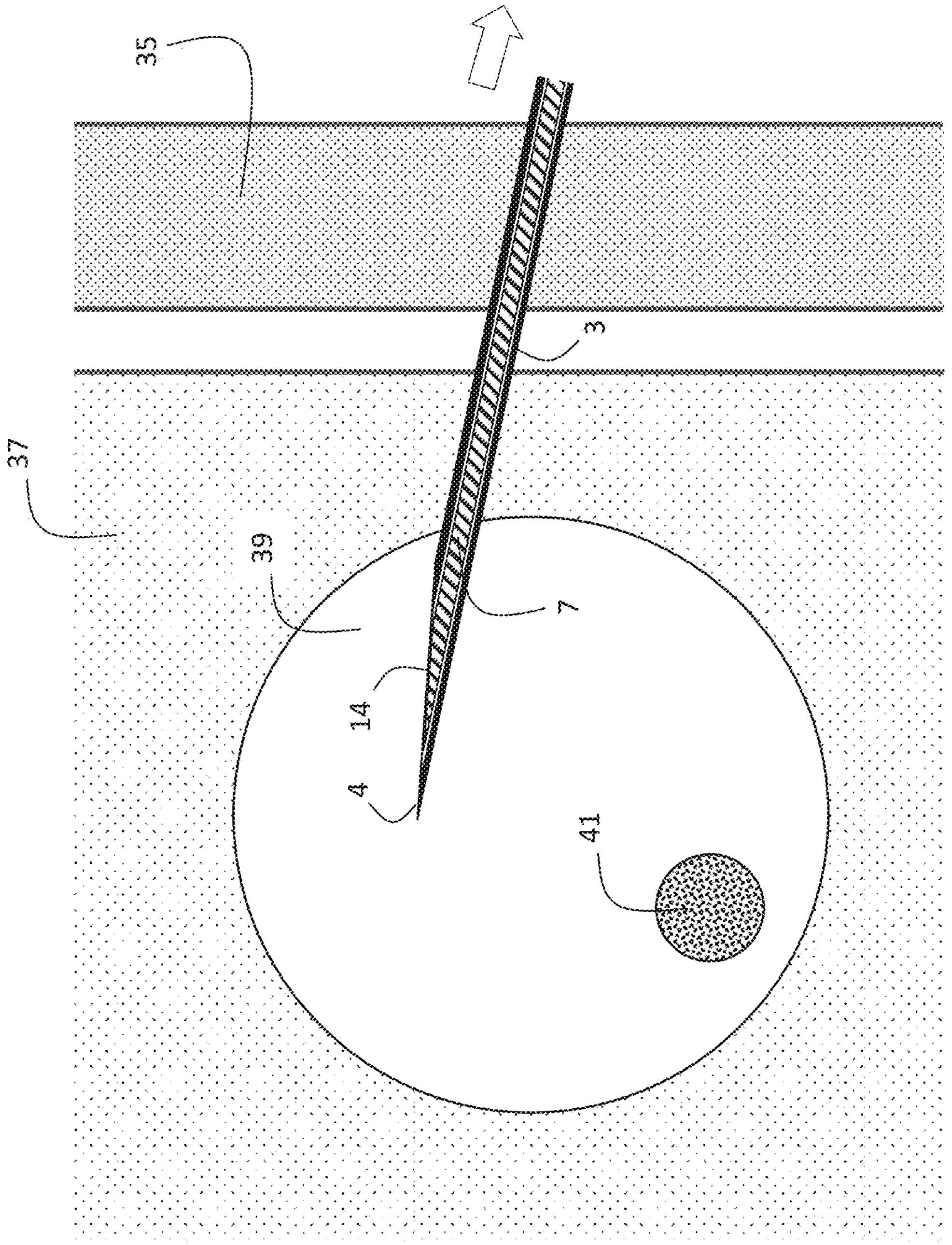

FIG. 4 shows how the biopsy element 3 with the light guide 7 in the locked distal position has been inserted into the shadowing 39 of the organ 37 at another angle. The biopsy element 3 may not have to be pulled entirely out of the skin 35 again, but maybe only out of the organ 37 or the shadowing 39. There too, the fluorescence endoscopy element 5 does not detect any fluorescence signal, as there is only benign tissue in front of the distal end 14 of the light guide 7.

Figure 5:
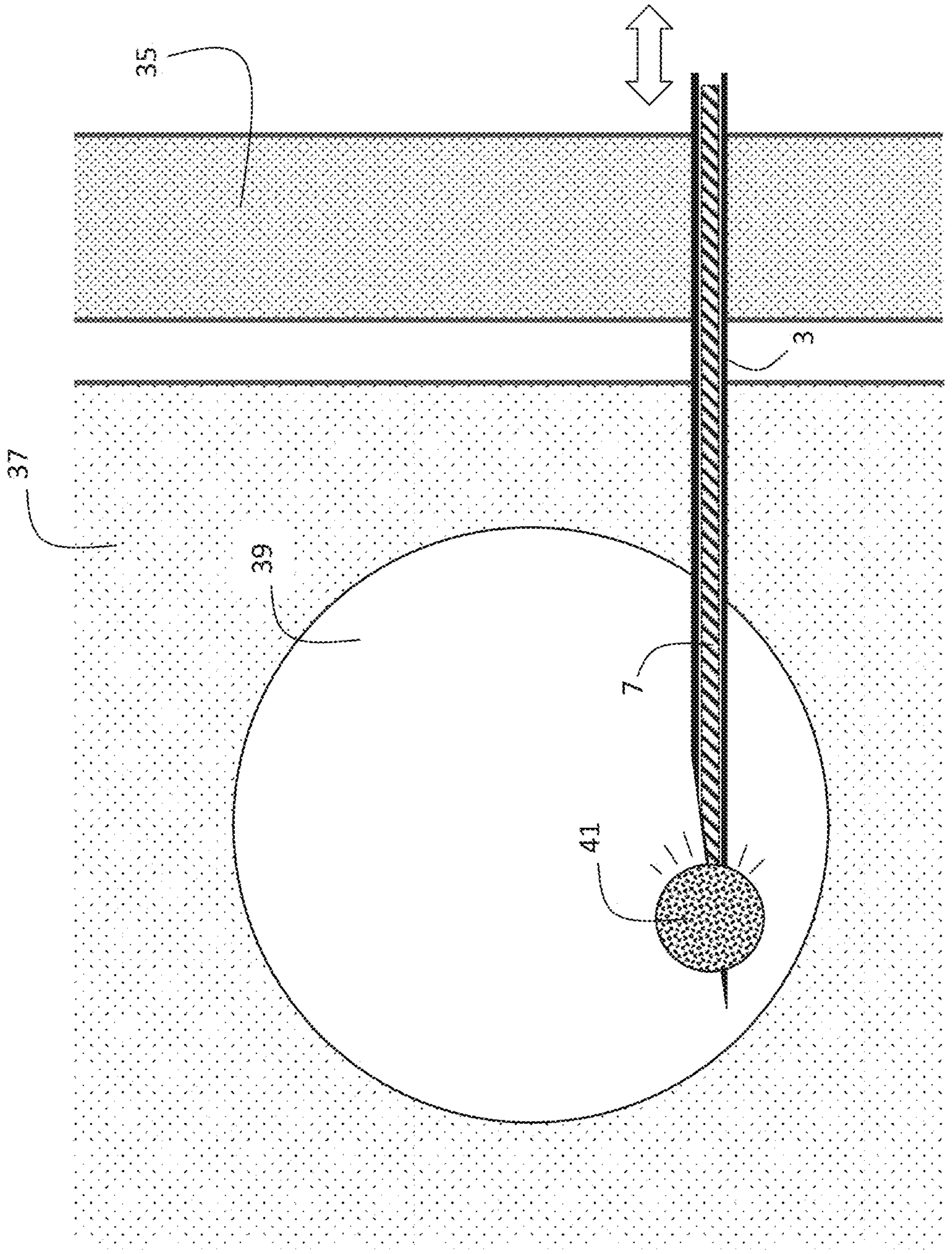
Figure 6:
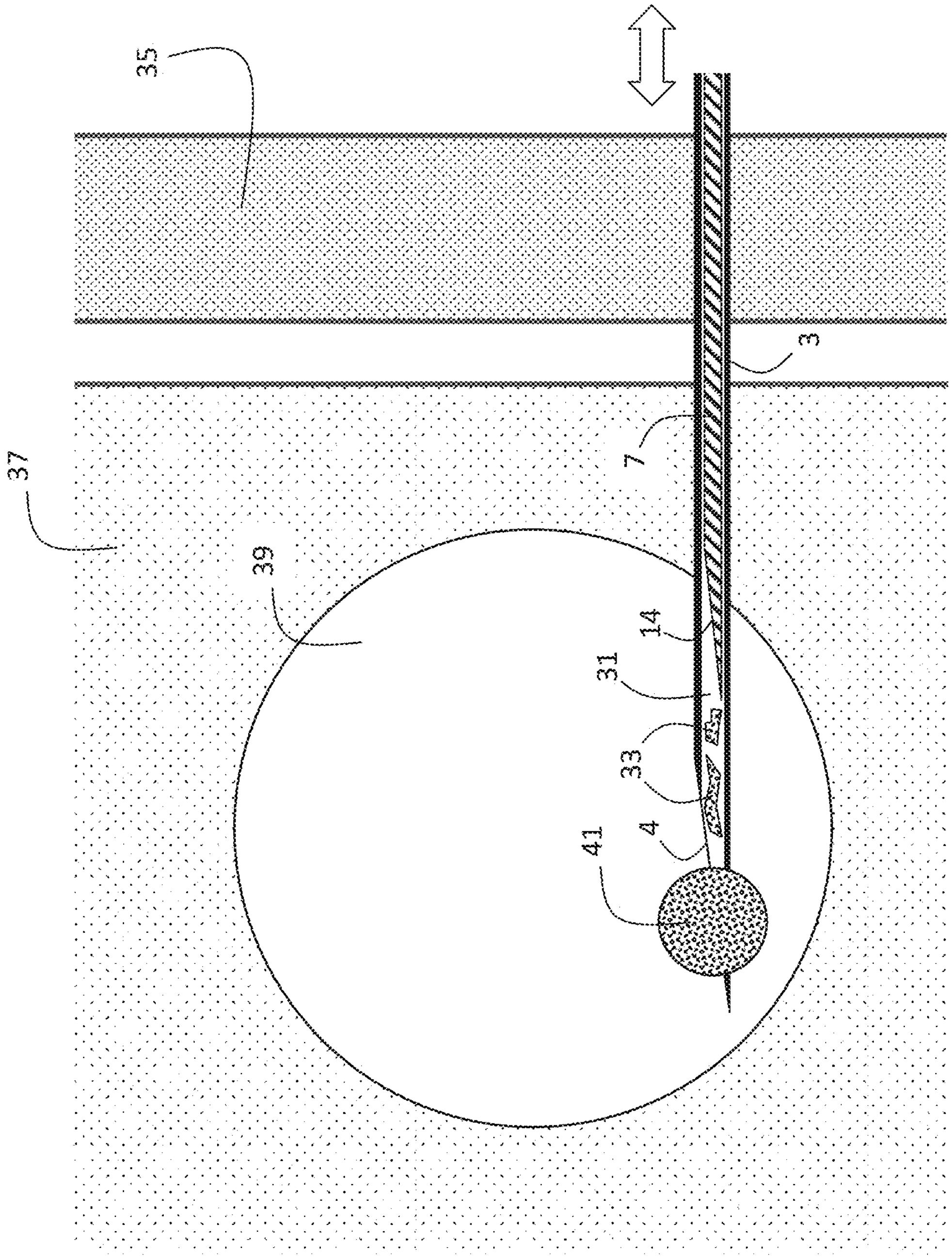

In FIG. 5 the operator has decided to insert the biopsy element 3 with the light guide 7 in the locked distal position through the skin 35 in a marginal area of the shadowing 39 at an entirely new place. That is where the malignant tissue 41 is located which conspicuously fluoresces through the influence of the stimulation light. If, in the opinion of the operator, the fluorescence signal is conspicuous enough, through moving forwards and backwards, malignant tissue 41 can be peeled off (FIG. 6). The operator then releases the locking of the light guide 7 and pulls this back proximally into a proximal position. The proximal position can be random or can be predetermined by a stop or a second lock. By pulling back the light guide 7, the receiving space 31 opens, wherein a sucking-in effect is produced with which a peeled off tissue sample 33 of malignant tissue 41 lying in front of the distal end 14 of the light guide 7 is sucked into the receiving space 31. Special attention is paid to the fact that the fluorescence signal remains conspicuous. This is because if it becomes strongly inconspicuous, this is a clear sign that no malignant tissue 41 or too little thereof is being sucked into the receiving space 31.

Figure 7:
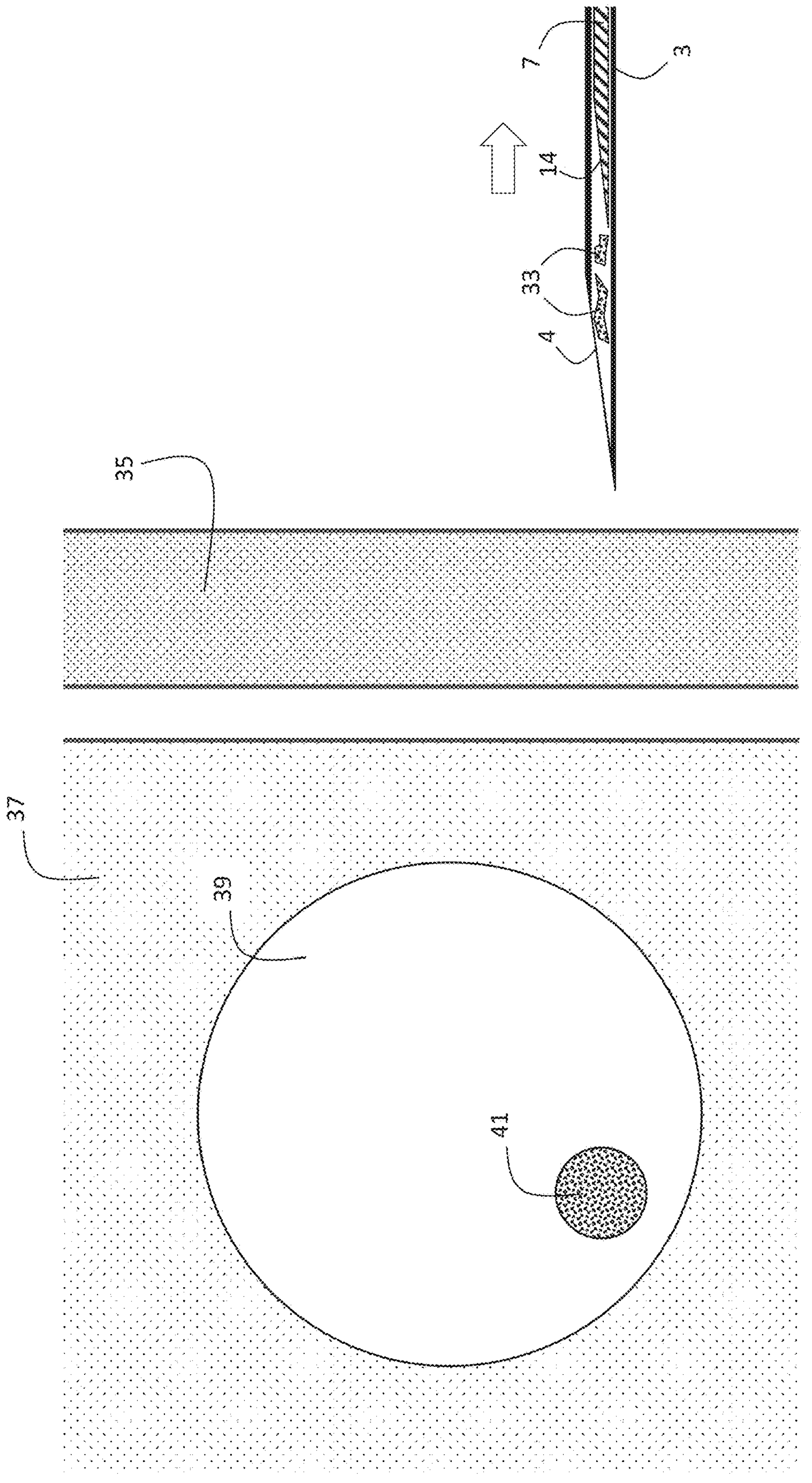

On finally pulling the biopsy element 3 out of the body of the patient, attention can be paid, as shown in FIG. 7, to the fluorescence signal remaining conspicuous enough. In this way if can, for example, be prevented that when pulling out, not fully peeled off tissue is pulled out of the receiving space 31 again unnoticed.

Figure 8:
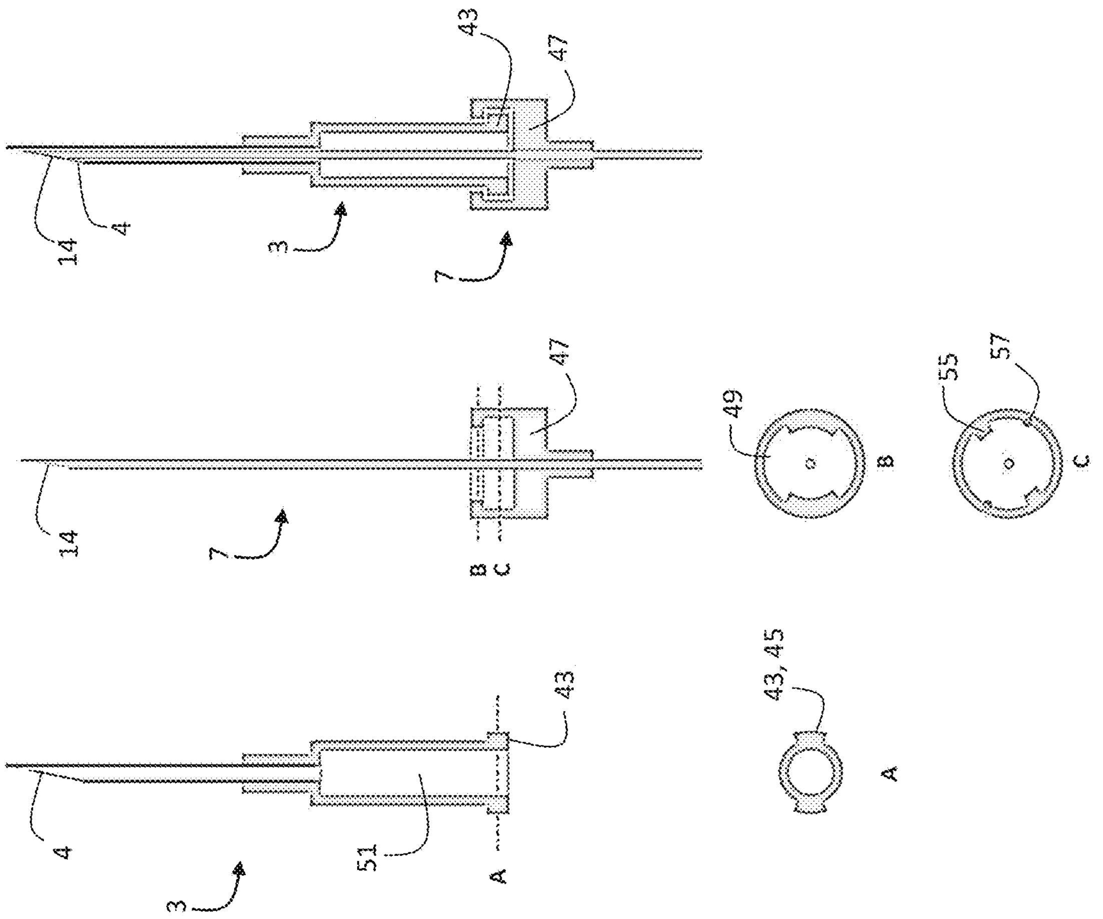
FIG. 8 shows schematic views of a first example of embodiment of a lock of a biopsy system disclosed herein.

In FIG. 8, a first form of embodiment of axial locking of the distal section 7 of the fluorescence endoscopy element 5 in the distal position relative to the biopsy element 3 is shown. For this, on the proximal side the biopsy element 3 has a locking flange 43. In the cross-sectional view A, it is evident that the locking flange 43 is not configured to be evenly circumferential, but is formed of two longitudinal bars 45. The distal section 7 of the fluorescence endoscopy element 5 has a female receiving section 47 complementary to the locking flange 43 that in its axial position is matched to the length of the biopsy element 3. In each of the two cross-sectional views B, C, the female receiving part 43 has a different cross-section contour with, in each case, longitudinal grooves 49 differently positioned in the circumferential direction through which the longitudinal bars 45 of the biopsy element 3 fit. Through corresponding rotary positioning, the locking flange 43 can thus be introduced into the receiving part 47 and then through turning locked therein. Preferably, the locking flange 43 and the receiving part 47 can be combined for secure, sealed and stable mechanical coupling with a Luer system, which has an inner cone 51 (here shown in simplified form as a cylinder) and a corresponding outer cone (of another component not shown here). The Luer system is preferably standardised and allows the use of already available biopsy elements. The axial position of the receiving part 47 in relation to the distal section 7 of the fluorescence endoscopy element 5 is determined so that in the case of the received and lock locking flange 43, the distal end 14 of the distal section 7 of the fluorescence endoscopy element 5 is closed flush with the distal tip 4 of the biopsy element 3. Provided in the cross-section contour C are radial stops 55, so that the rotary position of the bevelled distal tip 4 of the biopsy element 3 and of the correspondingly bevelled distal end 14 of the distal section 7 of the fluorescence endoscopy element 5 are matched to each other. An additional engaging function, e.g. through latches 57 on the inner side of the receiving section 47, can prevent the biopsy element 3 and the distal section 7 of the fluorescence endoscopy element 5, twisting with regard to each other along their common longitudinal axis when in use. This because the longitudinal bars 45 are engaged between the latches 57 and the radial stops 55. In the distal position, the distal section 7 of the fluorescence endoscopy element 5 is thus borne in a rotationally fixed manner about its longitudinal axis in the biopsy element 3 in a defined rotary position.

Figure 9:
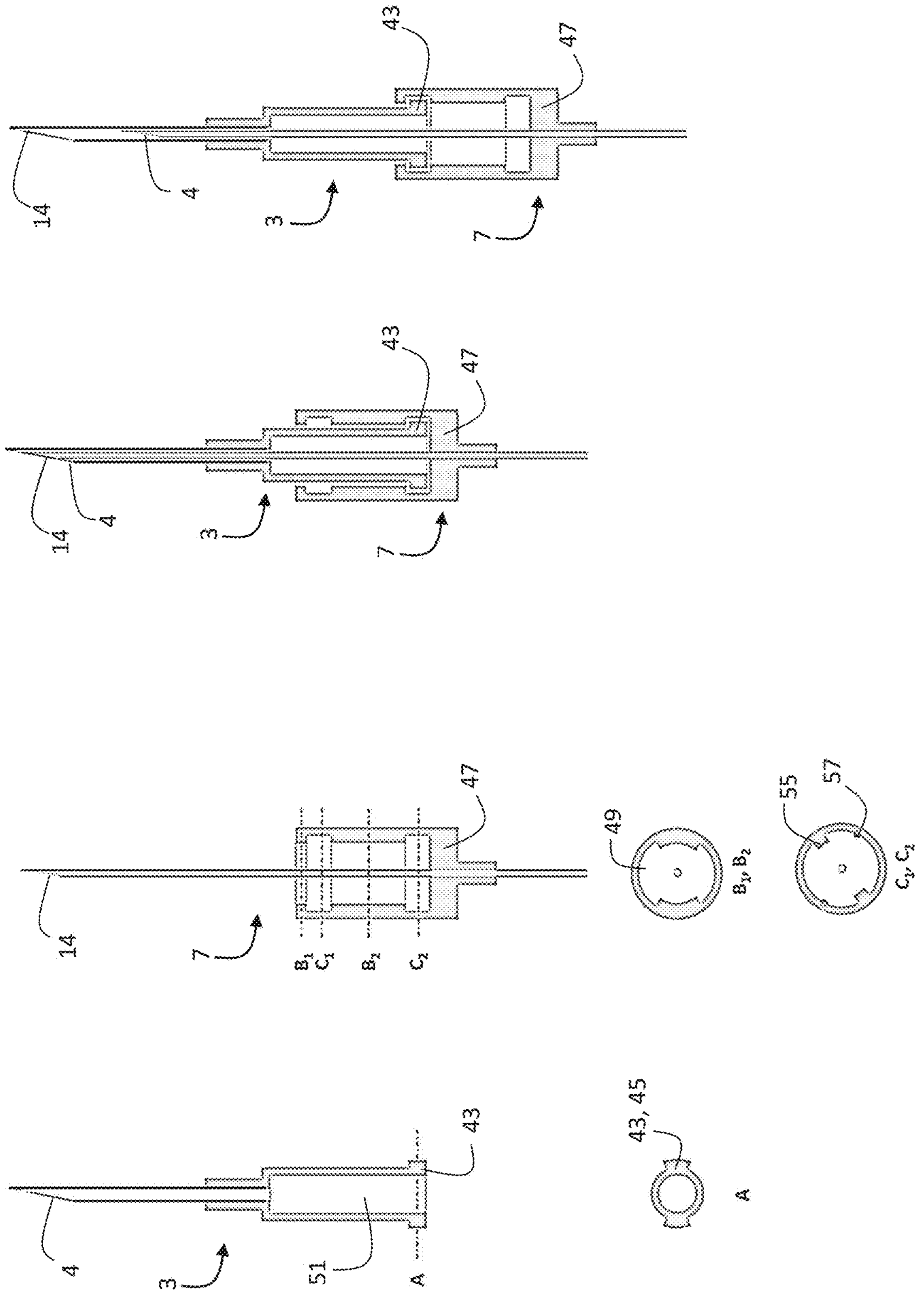
FIG. 9 shows schematic views of a second example of embodiment of a lock of a biopsy system disclosed herein.

In FIG. 9, a second form of embodiment with axial locking of the distal section 7 of the fluorescence endoscopy element 5 in both the distal position and also the proximal position relative to the biopsy element 3 is shown. In contrast to the first form of embodiment according to FIG. 8, the proximal position in the second form of embodiment is not random, but structurally predetermined. Here, the biopsy element 3 does not differ from the biopsy element 3 according to FIG. 8, i.e. it also has the locking flange 43 on the proximal side. The female receiving part 47 of the fluorescence endoscopy element 5 complementary to the locking flange 43, has cross-section contours $B_1$, $B_2$ and $C_1$, $C_2$ at axially different positions. The cross-section contour $C_1$ defines the distal position, and the cross-section contour $C_2$ defines the proximal position. The cross-section contours $B_1$, $B_2$ serve to lock the locking flange 43 into the respective axial positions $C_1$ and $C_2$. In an analogue manner to FIG. 8, through corresponding rotary positioning, the locking flange 43 can thus be axially moved into the receiving part 47 through the cross-section contours $B_1$, $B_2$ and through turning locked in axial positions $C_1$ und $C_2$. The axial position of the cross-section contour $C_2$ in relation to the distal section 7 of the fluorescence endoscopy element 5 is determined so that in the case of the received and locked locking flange 43 in cross-section contour $C_2$, the distal end 14 of the distal section 7 of the fluorescence endoscopy element 5 is closed flush with the distal tip 4 of the biopsy element 3. In the same way as in FIG. 8, in both the distal position $C_2$ and the proximal position $C_1$, the distal section 7 of the fluorescence endoscopy element 5 is thus borne by means of latches 57 and radial stops 55 in a rotationally fixed manner about its longitudinal axis in the biopsy element 3 in a defined rotary position.

The numbering of the components or movement directions as "first", "second", "third" etc. is purely arbitrarily selected to distinguish the components or movement directions from each other and can be selected in any other way. No order of priority is associated therewith. The designation of a component or technical feature as "first" should not be misunderstood to the effect that there has to be a second component or technical feature of this type. Moreover, any process steps, unless explicitly mentioned otherwise or absolute necessary, can be carried out in any order and/or partially or fully overlapping in time.

Equivalent forms of embodiment of the parameters, components or functions described herein, which in consideration of this description appear evident to a person skilled in the art, are included herein as if they have been explicitly described. Accordingly, the protective scope of the claims should cover such equivalent forms of embodiment. "Can" features designated as optional, advantageous, preferred, desired or similar are to be understood as optional and not as restricting the protective scope.

The described forms of embodiment are to be understood as illustrative examples and do not represent an exhaustive list of possible forms of embodiment. Each feature disclosed as part of a form of embodiment can be used alone or in combination with one or more other features, irrespective of in which form of embodiment the features have been described in each case. Whereas at least one example of embodiment is shown and described herein, derivations and alternative forms of embodiment that in consideration of this description appear evident to a person skilled in the art, are included in the protective scope of this disclosure. Furthermore, neither the term "comprise" should exclude additional, other features or process stages, nor should "a" or "an" exclude a plurality.

While specific embodiments of the invention have been shown and described in detail to illustrate the application of the principles of the invention, it will be understood that the invention may be embodied otherwise without departing from such principles.

LIST OF REFERENCE NUMBERS

1 Biopsy system
3 Biopsy element
4 Distal tip of the biopsy element

5 Fluorescence endoscopy element
7 Light guide or distal section of the fluorescence endoscopy element
9 Handpiece
11 Operating unit
13 Optical component
14 Distal end of the distal section of the fluorescence endoscopy element or light guide
15 Beam splitter
17 Longpass filter
19 Image sensor, photodiode or similar
21 Light source
23 Cable connection
25 Display component
27 Control and supply component
29 Operating component
31 Receiving space
33 Tissue sample
35 Skin of the patient
37 Organ of the patient
39 Shadowing
41 Malignant tissue
43 Locking flange
45 Longitudinal bars
47 Receiving section
49 Longitudinal grooves
51 Inner cone
55 Radial stops
57 Latches

The invention claimed is:

1. A biopsy system comprising:

a biopsy element for taking a sample of tissue to be examined from an organic body; and a fluorescence endoscopy element comprising a distal section with a decoupling of stimulation light and coupling of fluorescence light, wherein the distal section of the fluorescence endoscopy element is positioned in the biopsy element and is axially positionable in a distal position and in a proximal position, wherein for receiving the sample of the tissue to be examined, the biopsy element comprises a receiving space which in the distal position of the distal section of the fluorescence endoscopy element is distally closed and in the proximal position of the distal section of the fluorescence endoscopy element is distally open, wherein the distal section of the fluorescence endoscopy element comprises a radial seal which is configured to guide the distal section of the fluorescence endoscopy element in the biopsy element, such that in the receiving space, during a pulling back of the distal section of the fluorescence endoscopy element proximally in the biopsy element, a sucking-in effect is produced in the receiving space.

2. The biopsy system according to claim 1, wherein in the distal position the distal section of the fluorescence endoscopy element completely fills the receiving space.

3. The biopsy system according to claim 1, wherein the fluorescence endoscopy element is configured to distally extract stimulation light and inject fluorescence light in the distal position of the distal section of the fluorescence endoscopy element, the proximal position of the distal section of the fluorescence endoscopy element and/or any intermediate position of the distal section of the fluorescence endoscopy element.

4. The biopsy system according to claim 1, wherein a distal end of the distal section of the fluorescence endoscopy element in the distal position closes the receiving space in a flush manner with a distal tip of the biopsy element or distally projects from the distal tip of the biopsy element.

5. The biopsy system according to claim 1, wherein the distal section of the fluorescence endoscopy element is lockable in the distal position and/or the proximal position relative to the biopsy element.

6. The biopsy system according to claim 1, wherein a distal end of the distal section of the fluorescence endoscopy element is mounted rotationally fixed in a defined rotational position around a distal end longitudinal axis in the biopsy element, at least in a distal position.

7. The biopsy system according to claim 1, wherein a distal end of the distal section of the fluorescence endoscopy element and a distal tip of the biopsy element are bevelled at a same angle.

8. The biopsy system according to claim 7, wherein the angle is acute.

9. The biopsy system according to claim 1, wherein a distal end of the distal section of the fluorescence endoscopy element and/or the biopsy element is/are configured as a disposable article for single use.

10. The biopsy system according to claim 1, wherein the fluorescence endoscopy element comprises a light guide with proximal coupling in of stimulation light and/or proximal decoupling of fluorescence light, wherein a distal end of the light guide distally extracts the stimulation light and/or distally couples in the fluorescence light.

11. The biopsy system according to claim 1, wherein a distal end of the distal section of the fluorescence endoscopy element has a light-emitting diode for decoupling stimulation light and/or an image sensor or a photodiode for coupling in fluorescence light.

12. The biopsy system according to claim 1, wherein the fluorescence endoscopy element is configured to proximally inject a first stimulation light and/or a second stimulation light, wherein the first stimulation light is on average shorter wave than the second stimulation light, and wherein the fluorescence endoscopy element is configured to produce a first image or a first fluorescence signal of a first tissue area from the first fluorescence light stimulated with the first stimulation light and a second image or a second fluorescence signal from a second tissue area from the second fluorescence light stimulated with the second stimulation light.

13. The biopsy system according to claim 1, wherein proximally, the fluorescence endoscopy element comprises an optical component which is detachably coupleable or firmly coupled to the distal section of the fluorescence endoscopy element, wherein the optical component comprises a beam splitter with an image path side and an illumination path side, wherein to extract the fluorescence light an image sensor or a photodiode is detachably coupleable or firmly coupled to the image path side, and wherein to inject the stimulation light, a light source is detachably coupleable or firmly coupled to the illumination path side.

14. The biopsy system according to claim 13, wherein the optical component further comprises an optical longpass filter which transmits the fluorescence light more strongly to the image path side than the stimulation light, and/or comprises an optical shortpass filter which reflects the fluorescence light more strongly to the image path side than the stimulation light.

15. The biopsy system according to claim 14, wherein the fluorescence endoscopy element comprises an operating unit signal-connected or connectable with the image sensor or the photodiode and/or the light source, wherein the operating unit comprises an optical or acoustic display component, a control and supply component and an operating component.

16. The biopsy system according to claim 14, wherein the optical component is arranged in a handpiece of the fluorescence endoscopy element to which the distal section of the fluorescence endoscopy element and the biopsy element is/are connected and wherein the handpiece is configured for multiple use.

17. The biopsy system according to claim 13, wherein the fluorescence endoscopy element comprises an operating unit signal-connected or connectable with the image sensor or the photodiode and/or the light source, wherein the operating unit comprises an optical or acoustic display component, a control and supply component and an operating component.

18. The biopsy system according to claim 13, wherein the optical component is arranged in a handpiece of the fluorescence endoscopy element to which the distal section of the fluorescence endoscopy element and the biopsy element is/are connected.

19. The biopsy system according to claim 1, wherein the biopsy system is a system for fine-needle biopsy or fine-needle aspiration biopsy.

20. The biopsy system according to claim 1, wherein:

the fluorescence endoscopy element is configured to indicate a level of a fluorescence signal detected by the fluorescence endoscopy element with the distal section of the fluorescence endoscopy element disposed at the distal position of the distal section of the fluorescence endoscopy element;

the fluorescence endoscopy element is configured to indicate a level of the fluorescence signal detected by the fluorescence endoscopy element with the distal section of the fluorescence endoscopy element disposed between the distal position of the distal section of the fluorescence endoscopy element and the proximal position of the distal section of the fluorescence endoscopy element;

the fluorescence endoscopy element is configured to indicate a level of the fluorescence signal detected by the fluorescence endoscopy element with the distal section distal section of the fluorescence endoscopy element disposed at the proximal position of the distal section of the fluorescence endoscopy element; and the fluorescence endoscopy element is configured to indicate a weakening of the fluorescence signal during movement of the distal section of the fluorescence endoscopy element between the distal position of the distal section of the fluorescence endoscopy element and the proximal position of the distal section of the fluorescence endoscopy element and/or the fluorescence endoscopy element is configured to indicate a compliance with a defined lower limit for the fluorescence signal with the distal section of the fluorescence endoscopy element at the distal position of the distal section of the fluorescence endoscopy element, with the distal section of the fluorescence endoscopy element disposed between the distal position of the distal section of the fluorescence endoscopy element and the proximal position of the distal section of the fluorescence endoscopy element, and with the distal section of the fluorescence endoscopy element disposed at the proximal position of the distal section of the fluorescence endoscopy element.

* * * * *